United States Patent [19]

Allan et al.

[11] Patent Number: 4,649,139
[45] Date of Patent: Mar. 10, 1987

[54] 1,2,4-TRIAZINES

[75] Inventors: Geoffrey Allan, London; Alistair A. Miller, Tonbridge; David A. Sawyer, Hayes, all of England

[73] Assignee: Burroughs Wellcome Co., Research Triangle Park, N.C.

[21] Appl. No.: 663,682

[22] Filed: Oct. 22, 1984

[30] Foreign Application Priority Data

Oct. 27, 1983 [GB] United Kingdom ............... 8328757

[51] Int. Cl.$^4$ ................... C07D 253/06; A61K 31/53
[52] U.S. Cl. .................................. 514/242; 544/182
[58] Field of Search ...................... 544/182; 514/242

[56] References Cited

U.S. PATENT DOCUMENTS 3,637,688  1/1972  Rees et al. ..................... 544/182
3,752,808  8/1973  Jautelat et al. ................. 544/182

FOREIGN PATENT DOCUMENTS 21120    4/1983  European Pat. Off. .
77983    5/1983  European Pat. Off. .
759014   2/1953  United Kingdom .
1248262  9/1971  United Kingdom .

Primary Examiner—John M. Ford
Attorney, Agent, or Firm—Donald Brown

[57] ABSTRACT

Compounds of Formula I are novel and useful as cardiovascular agents, particularly anti-arrhythmic agents:

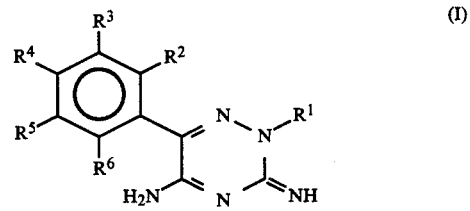

or the 5-imino-tautomer thereof or a salt of either, wherein $R^1$ is $C_{1-10}$ alkyl, $C_{2-10}$ alkenyl, $C_{2-10}$ alkynyl or $C_{3-10}$ cycloalkyl, any of which is optionally substituted, and $R^2$ to $R^6$ are independently selected from hydrogen, halogen atom, $C_{1-6}$ alkyl, alkenyl or alkynyl (all optionally substituted by one or more of halogen, hydroxy and aryl, amino, mono- or di-substituted amino, alkoxy (optionally substituted by one or more of halogen, hydroxy and aryl), alkenyloxy, aryl, acyloxy, cyano, nitro, aryl and alkylthio groups or any adjacent two of $R^2$ to $R^6$ are linked to form a (—CH=CH—CH=CH—) group.

20 Claims, No Drawings

1,2,4-TRIAZINES

The present invention relates to the chemotherapy of cardiac disorders such as arrhythmias.

U.K. Pat. No. 759,014 discloses compounds of the formula (A):

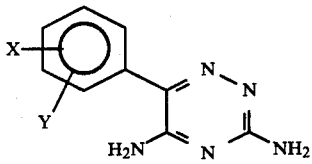
(A)

wherein X and Y are hydrogen and/or halogen atoms, as having activity against bacterial and malarial infections in animals. European Patent Publication No. 21 121 discloses that novel compounds of the formula (A), wherein x is chlorine, bromine, iodine, $C_{1-4}$ alkyl or trifluoromethyl at the 2-position of the phenyl ring and Y is hydrogen (other than when X is chlorine) or one or more defined substituents at other positions of the phenyl ring, have useful activity in the treatment of CNS disorders, particularly epilepsy. European Patent Publication No: 24 351 discloses that known compounds of the formula (A) wherein X is a 2-chloro atom and Y is a hydrogen atom or a 4-chloro atom or X and Y are 3- and 4-chloro atoms respectively have useful activity in the treatment of CNS disorders, particularly epilepsy.

U.K. Pat. No: 1248262 discloses inter alia compounds of the formula (B):

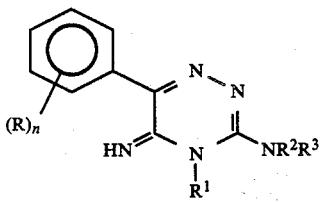
(B)

wherein: R is halogen, trifluoromethyl, cyano, thiocyanate, nitro, lower alkyl, lower alkoxy or lower alkylmercapto; n=0,1,2 or 3; $R^1$ is lower aliphatic hydrocarbyl, amino, lower alkylamino or lower dialkylamino; $R^2$ is lower aliphatic hydrocarbyl, and $R^3$ is lower aliphatic hydrocarbyl or hydrogen. It is disclosed that these compounds have strong herbicidal properties.

European Patent Publication No. 77 983 discloses, as being useful as anti-hypotensive and anti-thrombotic agents, compounds of Formulae C, D and E:

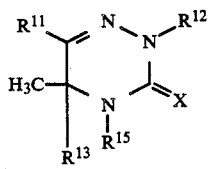
(C)

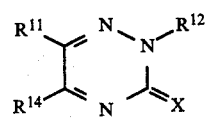
(D)

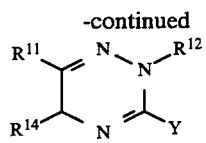
(E)

wherein $R^{11}$ is (inter alia) aryl; $R^{12}$ and $R^{15}$ are (inter alia) lower alkyl; $R^{13}$ is hydrogen, lower alkyl or aralkyl; $R^{14}$ is lower alkyl; X is oxygen or sulphur; and Y is (inter alia) amino, hydrazino or amidino.

It has now been discovered that a group of novel 5(or 3)-amino-6-(substituted phenyl)-2,3 (or 2,5) -dihydro-3(or 5)-imino-2-alkyl-1,2,4-triazines are active in the treatment of cardiac disorders, and are particularly useful in the treatment of arrhythmias.

Accordingly, the present invention provides a compound of formula (I):

(I)

or the 5-imino tautomer thereof or a salt of either, wherein $R^1$ is $C_{1-10}$ alkyl, $C_{2-10}$ alkenyl, $C_{2-10}$ alkynyl or $C_{3-10}$ cycloalkyl, any of which is optionally substituted, and $R^2$ to $R^6$ are independently selected from hydrogen, halogen, $C_{1-6}$ alkyl, alkenyl, alkynyl or alkoxy (all optionally substituted by one or more of halogen, hydroxy and aryl), amino, mono- or di-substituted amino, alkenyloxy, acyl, acyloxy, cyano, nitro, aryl and alkylthio groups or any adjacent two of $R^2$ to $R^6$ are linked to form a (—CH=CH—CH=CH—) group.

Clearly, when an acid addition salt is formed, the 4-nitrogen is protonated and the compound assumes the 3,5-diamino configuration.

Suitably $R^1$ is an unsubstituted $C_{1-6}$ alkyl group. Methyl, isopropyl and n-propyl are particularly preferred.

Suitably the total number of carbon atoms in $R^2$ to $R^6$ is less than eight.

The phenyl ring will suitably contain up to three substituents and preferably one or two substituents. It is preferred that there is a substituent at the 2-position of the phenyl ring.

$R^2$ to $R^6$ are preferably selected from halogen or $C_{1-7}$ alkoxy groups. Particularly preferred substitutions are 2,3 or 2,5 or 2,3,5 di- or tri-halo (especially chloro) and 2-pentyloxy.

Preferred compounds are: 5(3)-amino-6-(2,3-dichlorophenyl)-2,3(2,5)-dihydro-3(5)-imino-2-isopropyl-1,2,4-triazine; 5(3)-amino-6-(2,3,5-trichlorophenyl)-2,3(2,5)-dihydro-3(5)-imino-2-methyl-1,2,4-triazine; 5(3-amino-6-(2,3-dichlorophenyl)-2,3(2,5)-dihydro-3(5)-imino-2-n-propyl-1,2,4-triazine; and 5(3)-amino-6-(2-pentyloxphenyl)-2,3(2,5)-dihydro-3(5)-imino-2-methyl-1,2-triazine.

Preferred salts of the present invention are pharmaceutically acceptable acid addition salts but other salts, such as those useful in the preparation of compounds of the formula I, are also included within the scope of the present invention. Suitable pharmaceutically acceptable acid addition salts include those formed with both organic and inorganic acids, for example from hydrochloric, sulphuric, citric, tartaric, phosphoric, lactic, pyruvic, acetic, malonic, succinic, oxalic, fumaric, maleic, oxaloacetic, methanesulphonic, p-toluenesulphonic, benzenesulphonic, glutamic, naphthoic and isethionic acids.

The present invention also provides the first medical use of the compounds of formula I as hereinbefore defined. Preferably this will be for the treatment of cardiovascular disorders, and in particular arrhythmias in humans. More specifically, compounds of formula I have been found to be potentially useful in the prophylaxis and treatment of chronic ventricular tachyarrhythmias, unifocal and multi-focal extrasystoles, or similar conditions with accessory pathway involvement. Such arrhythmias may result from cardiac infarction and are often chronic conditions.

In a further aspect, the present invention provides pharmaceutical formulations comprising a compound of formula I in admixture with a pharmaceutically acceptable carrier. The compounds of formula I will be present in the compositions of the present invention in an effective unit dosage form, that is to say in an amount sufficient to be effective against cardiac disorders in vivo.

The pharmaceutically acceptable carriers present in the compositions of the present invention are materials recommended for the purpose of administering the medicament. These may be liquid or solid materials, which are otherwise inert or medically acceptable and are compatible with the active ingredients.

These pharmaceutical compositions may be given orally or parenterally, for example as a suppository, ointment, cream, powder or trans-dermal patch. However, oral administration and intravenous injection of the compositions are preferred.

For oral administration, fine powders or granules will contain diluting, dispersing and/or surface active agents, and may be presented in draught, in water or in a syrup, in capsules or sachets in the dry state or in non-aqueous suspension wherein suspending agents may be included, or in a suspension in water or syrup. Where desirable or necessary, flavouring, preserving, suspending, thickening or emplifying agents can be included. Dry powder or granules may be compressed to form a tablet or contained in a capsule.

For injection, the compounds may be presented in sterile aqueous injection solutions which may contain anti-oxidants or buffers.

As stated above, the free base or a salt thereof may be administered in its pure form unassociated with other additives in which case a capsule or sachet is the preferred carrier.

Alternatively the active compound may be presented in a pure form as an effective unit dosage, for instance compressed as a tablet or the like.

Other compounds which may be included are, for example, medically inert ingredients, e.g., solid and liquid diluents such as lactose, starch, or calcium phosphate for tablet or capsules; olive oil or ethyl oleate for soft capsules; and water or vegetable oil for suspensions or emulsions; lubricating agents such as talc or magnesium stearate; gelling agents such as colloidal clays; thickening agents such as gum tragacanth or sodium alginate; and other therapeutically acceptable accessary ingredients such as humectants, preservatives, buffers, and antioxidants which are useful as carriers in such formulations.

Tablets or other forms of presentation provided in discrete units may conveniently contain an amount of compound of formula I which is effective at such dosage or as a multiple of the same, for instance units containing 5 mg to 500 mg, usually around 10 mg to 250 mg.

The pharmaceutical compositions of the present invention will be prepared by the admixture of a compound of formula I with a pharmaceutically acceptable carrier. Conventional pharmaceutical excipients may be admixed as required.

The present invention provides a method of treatment of cardiac disorders in mammals, and particularly arrhythmias in humans, by the administration of a non-toxic effective amount of a compound of formula I or a pharmaceutically acceptable salt, or a composition as hereinbefore defined.

As indicated above, the compounds of formula I are generally useful in treating such disorders by oral administration or intravenous injection.

The compounds of formula I are normally administered at a dose of from 0.01 mg/kg. to 20 mg/kg. per day, preferably 0.1 to 5.0 mg/kg per day. The dose range for adult humans is thus generally from 0.7 mg to 1400 mg/day and preferably 7 to 350 mg/day.

The present invention also provides the following processes for preparing the compounds of formula I:

(a) the alkylation, aralkylation etc, as appropriate of a compound of formula II by use of a compound of formula III:

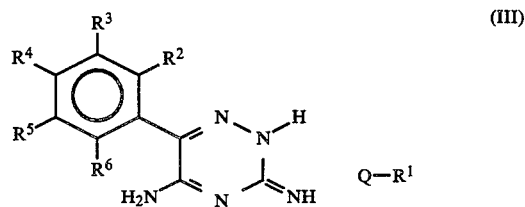

where Q is a leaving group such as halogen or a derivative of sulphonic acid (for example alkylsulphonyloxy, arylsulphonyloxy or aralkylsulphonyloxy) and $R^1$ to $R^6$ are as defined above. Although, for clarity, the compound of formula II is shown as having a hydrogen at the 2-position, in practice the hydrogen will "shift" to form the 3-amino tautomer:

(b) by ring closure of a compound of formula (IV):

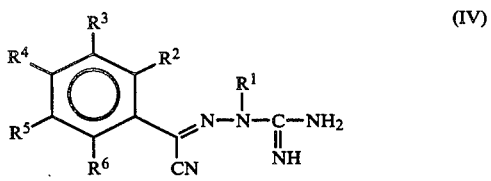

(c) by reaction of a compound of formula (V) with ammonia or an ammonium salt:

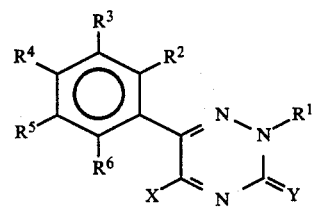

(V)

where X is a leaving group such as halogen, alkoxy or a derivative of sulphonic acid as above and Y is a leaving group such as oxygen or sulphur. The positions of X and Y may be reversed;

(d) by reduction of an amine precursor group, such as an azide, on a compound of formula (VI):

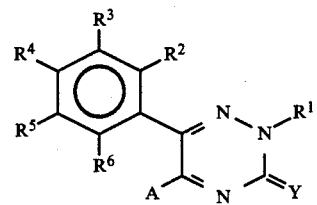

(VI)

wherein A is the amine precursor group and Y is as defined for formula (V) above. The positions of the amine precursor group and Y may be reversed;

(e) by the removal of a protecting group from a compound of formula (VII) or (VIII):

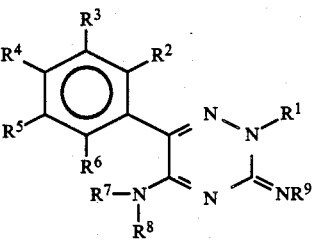

(VII)

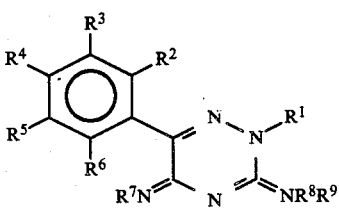

(VIII)

wherein at least one of $R^7$, $R^8$ and $R^9$ is a protective group such as benzyl group.

The alkylation etc of the compound of formula II will take place under conventional conditions in a suitable polar solvent in which the said compound of formula II is soluble at a non-extreme temperature (for example between 0° and 100° C. and conveniently at room temperature). The compound of formula II is, for example, prepared by the method of European Patent Publication No. 21 121.

Reaction (b) will normally be carried out in anhydrous conditions with a base catalyst such as sodium methoxide.

Reaction (c) will normally be carried out at 0°–150° C. in a non-aqueous solvent.

Suitable reducing agents for reaction (d) include lithium aluminium hydride in non-aqueous conditions.

The de-protection of reaction (e) may conveniently be achieved by hydrogenation over a suitable catalyst.

The compound of formula (IV) may be made by reaction of a compound of formula (IX) with a compound of formula X:

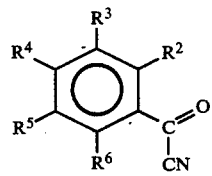

(IX)

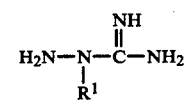

(X)

The compound of formula X may be made either from a compound of formula XI by the method of Bream J. B. et al, J. Med. Chem. 1970 vol 13(b) 105 or by reduction of the corresponding nitroso derivative, formula XII:

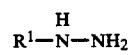

(XI)

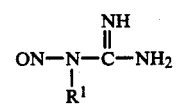

(XII)

The compound of formula XII may be made by reaction of nitrous acid and a guanidine derivative of formula XIII:

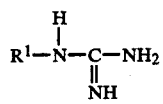

(XIII)

The invention also provides novel intermediates of formulae II to XIII above, in particular those of formula II. For example, compounds of formula II are believed to be novel when $R^2$ to $R^6$ are as defined above, but other than hydrogen, $C_{1-4}$ alkyl or halogen.

The following Examples illustrate the preparation of compounds of the invention and their use in the treatment of cardiac disorders.

CHEMICAL EXAMPLES

EXAMPLE 1

Preparation of 5(3)-Amino-6-(2,3-dichlorophenyl)-2,3(2,5)-dihydro-3(5)-imino-2-methyl-1,2,4-triazine 2,3-Dichlorobenzoic Acid: A solution of 2,3-dichloroiodobenzene (37.3 g, 0.14M) in sodium dried ether (300 ml) was added dropwise to magnesium turnings (3.65 g, 0.15 gm Atm) and a crystal of iodine with warming so as to form a Grignard reagent. The mixture was stirred and heated to reflux for 2 hours, then cooled and transferred dropwise, under nitrogen, into a stirred mixture of sodium dried ether (250 ml) containing solid carbon dioxide (ca. 100 g). The mixture was stirred for 2 hours, left overnight to warm to room temperature, then treated with ice (ca. 150 g) and 2N aqueous hydrochloric acid (75 ml), and the product extracted with ether (200, 100 and 50 ml). The combined ether extracts were wased with water (2×40 mls) then repeatedly extracted with 2N aqueous sodium hydroxide (100, 50 and 50 mls). These basic solutions were combined, stirred with activated charcoal (3 g) for 10 minutes, filtered and the cooled filtrate was acidified with concentrated hydrochloric acid (25 ml) at 10° C. The resultant solid was filtered off, washed with water (2×20 ml) and dried in vacuo. Yield 20.76 g (77.6%), m.p. 167°–169° C. (uncorrected).

2,3-Dichlorobenzoyl Chloride: A mixture of 2,3-dichlorobenzoic acid (39.4 g 0.2M) and thionyl chloride (100 ml) was heated to reflux for 2½ hours. The cooled solution was evaporated down in vacuo and distilled under nitrogen. Yield 35.5 g (85%), b.p. 146°–148° C. at 31 mm of mercury pressure.

2,3-Dichlorobenzoyl Cyanide: A mixture of cuprous cyanide (36.9 g, 0.41M), potassium iodide (68.5 g, 0.41M) and xylene (400 mls) was heated to reflux in an atmosphere of nitrogen under a Dean and Stark trap for 24 hours so as to remove all trace of water. A solution of 2,3-dichlorobenzoyl chloride (35.5 g, 0.17M) in sodium dried xylene (130 ml) was added dropwise to the above mixture of dry cuprous cyanide and xylene. The resulting mixture was stirred and heated to reflux for a further 72 hours. The cooled mixture was filtered and the solid washed well with sodium dried xylene (200 ml). The filtrate and washings were combined and evaporated down in vacuo to give an oil. Yield 32 g (94%).

3,5-Diamino-6-(2,3-dichlorophenyl)-1,2,4-triazine: A solution of 2,3-dichlorobenzoyl cyanide (32 g, 0.16M) in dimethylsulphoxide (80 ml) was added dropwise to a stirred suspension of aminoguanidine bicarbonate (81.67 g. 0.6M) which had been treated with 8N aqueous nitric acid (400 ml) at a temperature of ca 25° C. The mixture was stirred for 3 hours, then left to stand at room temperature for 7 days. The cooled mixture was stirred and basified with 0.880 aqueous ammonia (400 ml) at 20° C., then stirred with ice cooling for 30 minutes. The resulting solid was separated by filtration, washed thoroughly with water and finally dried in vacuo. The above solid was added to a 10% w/v solution of potassium hydroxide pellets in methanol (400 ml) and the solution heated to reflux for 1½ hours. When cool the solution was evaporated down in vacuo, treated with ice water (800 ml) then stirred for 30 minutes and filtered. The residue was dried and recrystallised from isopropanol to give 3,5-diamino-(2,3-dichlorophenyl)-1,2,4-triazine Yield 6.8 g (15.6%), m.p. 216°–218° C. (uncorrected).

5(3)-Amino-6-(2,3-dichlorophenyl)-2,3(2,5)-dihydro-3(5)-imino-2-methyl-1,2,4-triazine: A mixture of 3,5-diamino-6-(2,3-dichlorophenyl)-1,2,4-triazine (2.56 g, 10 mM) and methyl iodide (1.6 g, 11 mM) in acetone (200 ml) was stirred at 21° for 3 days then was evaporated to dryness in vacuo at 40°. The residue was treated with ice (ca. 50 g) followed by 0.880 aqueous ammonia solution (100 ml) and the whole was stirred for 30 min. The solid was separated by filtration, dried in vacuo and then recrystallised from methanol to give the title compound. Yield 1.56 g (58%), m.p. 228°–230° (uncorrected). N.M.R. (Me$_2$SO-d$_6$) δ7.70–7.37 (3H, m, ArH), 6.62 (3H, br s, NH) and 3.47 (3H, s, NMe); $^1$H coupled $^{13}$C N.M.R. [Me$_2$SO-d$_6$] 154.2 ppm (singlet), 153.7 ppm (quartet); MS m/z 269 (M+), 199 (M+—CN$_4$H$_2$) and 98

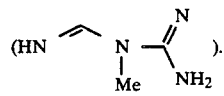

Analysis: Calcd. for C$_{10}$H$_9$Cl$_2$N$_5$: C, 44.46; H, 3.36; N, 25.93, Found: C, 44.61; H, 3.25; N, 25.63.

Example 2

Preparation of 5(3)-Amino-6-(2,5-dichlorophenyl)-2,3(2,5)-dihydro-3(5)-imino-2-methyl-1,2,4-triazine The hydriodide salt of the title compound was prepared from 3,5-diamino-6-(2,5-dichlorophenyl)-1,2,4-triazine in an analogous way to the method of Example 1 and then the base was isolated as in Example 1. This was converted into the mesylate salt by treatment with methanesulphonic acid (1.2 ml) in methanol (100 ml). The resulting solution was evaporated to dryness in vacuo and the residue was recrystallised from methanol to give the title compound. Yield 0.93 g (35%), m.p. 306°–308° (uncorrected).

Example 3

Preparation of 5(3)-Amino-6-(2-n-pentyloxyphenyl)-2,3(2,5)-dihydro-3(5)-imino-2-methyl-1,2,4-triazine The mesylate salt hemihydrate was prepared as in Example 2. Yield 1.76 g (45%), m.p. 192°–195° (uncorrected).

Example 4

Preparation of 5(3)-Amino-6-(2,3-dichlorophenyl)-2,3(2,5)-dihydro-3(5)-imino-2-isopropyl-1,2,4-triazine A suspension of 3,5-diamino-6-(2,3-dichlorophenyl)-1,2,4-triazine (2.56 g, 10 mM) and isopropyl iodide (2 ml, 20 mM) in acetone (200 ml) was stirred and heated to reflux for 7 days. The resulting suspension was cooled and the solid isolated by filtration. Treatment of this solid with 0.880 aqueous ammonia gave the base, which was converted into the mesylate salt monohydrate using the method described in Example 2. The product was recrystallised from 95% ethanol. Yield 500 mg (12%), m.p. 251°–252° (uncorrected).

Examples 5 to 18

By processes analogous to those given above in Examples 1 to 4, the following compounds were prepared.

Example 5

5(3)-Amino-6-phenyl-2,3(2,5)-dihydro-3(5)-imino-2-methyl-1,2,4-triazine was prepared as the mesylate salt monohydrate; m.p. 248°–250° C.

Example 6

5(3)-Amino-6-(2-chloro-6-fluorophenyl)-2,3(2,5)-dihydro-3(5)-imino-2-methyl-1,2,4-triazine was prepared as the hydrochloride (0.3H$_2$O) salt; m.p. 296°–298° C.

Example 7

5(3)-Amino-6-(2-iodophenyl)-2,3(2,5)-dihydro-3(5)-imino-2-methyl-1,2,4-triazine was prepared as the mesylate salt; m.p. 255°–256° C.

Example 8

5(3)-Amino-6-(2-methoxyphenyl)-2,3(2,5)-dihydro-3(5)-imino-2-methyl-1,2,4-triazine was prepared as the mesylate salt monohydrate; m.p. 213°–216° C.

Example 9

5(3)-Amino-6-(2-chlorophenyl)-2,3(2,5)-dihydro-3(5)-imino-2-methyl-1,2,4-triazine was prepared as the mesylate salt; m.p. 245°–247° C.

Example 10

5(3)-Amino-6-(2,3-dichlorophenyl)-2,3(2,5)-dihydro-3(5)-imino-2-n-propyl-1,2,4-triazine was prepared as the mesylate salt; m.p. 265°–266° C.

Example 11

5(3)-Amino-6-(2,4-dichlorophenyl)-2,3(2,5)-dihydro-3(5)-imino-2-methyl-1,2,4-triazine was prepared as the mesylate salt; m.p. 290°–292° C.

Example 12

5(3)-Amino-6-(2,3-dichlorophenyl)-2,3(2,5)-dihydro-3(5)-imino-2-benzyl-1,2,4-triazine was prepared as the mesylate salt; m.p. 269°–271° C. (dec.)

Example 13

5(3)-Amino-6-(2,3,5-trichlorophenyl)-2,3(2,5)-dihydro-3(5)-imino-2-methyl-1,2,4-triazine was prepared as the mesylate salt; m.p. 302°–304° C.

Example 14

5(3)-Amino-6-(4-n-pentyloxyphenyl)-2,3(2,5)-dihydro-3(5)-imino-2-methyl-1,2,4-triazine was prepared as the mesylate salt; m.p. 195°–200° C.

Example 15

5(3)-Amino-6-(2-n-propylphenyl)-2,3(2,5)-dihydro-3(5)-imino-2-methyl-1,2,4-triazine was prepared as the mesylate salt; m.p. 238°–240° C.

Example 16

5(3)-Amino-6-(2-n-propyloxyphenyl)-2,3(2,5)-dihydro-3(5)-imino-2-methyl-1,2,4-triazine was prepared as the hydrochloride; m.p. 278°–279° C.

Example 17

5(3)-Amino-6-(2-n-heptyloxyphenyl)-2,3(2,5)-dihydro-3(5)-imino-2-methyl-1,2,4-triazine was prepared as the hydrochloride; m.p. 247°–249° C.

Example 18

5(3)-Amino-6-(2,3-dichlorophenyl)-2,3(2,5)-dihydro-3(5)-imino-2-n-pentyl-1,2,4-triazine was prepared as the mesylate salt (0.66 H$_2$O); m.p. 203°–205° C. As the base was found to be unstable, the mesylate was prepared directly from the hydroiodide in an ion exchange column.

BIOLOGICAL EXAMPLES

Example A

Anaesthetised Rat Preparation

Male Wistar rats weighing 200–300 g were used. Anaesthesia was induced with a halothane:air mixture and maintained by intravenous administration of a chloralose/pentobarbitone sodium mixture (3 mg/ml pentobarbitone sodium+9.5 mg/ml chloralose) after insertion of a femoral vein cannula. A tracheal cannula was inserted and the animal was respired via a Palmer small animal respiration pump (72 strokes/min and approx 1 ml/100 g). Rectal temperature was thermostatically maintained at 37° C. throughout the experiment. Cannulae were placed in a jugular vein for administration of aconitine and a carotid artery for continuous measurement of blood pressure. Subdermal needle electrodes were inserted for the recording of electrocardiograms throughout the experiment.

When the blood pressure of the animal had stabilised for 10–15 minutes, aconitine (dissolved in distilled water+HCl and diluted in 5% dextrose) was infused via the jugular vein cannula at a rate of 1 μg/min (0.03 mls/min). The total dose of aconitine required to produce ventricular tachycardia or ventricular fibrillation (VT/VF) of at least 1 sec duration was taken as the endpoint of the assay.

Anti-arrhythmic activity was assessed by pretreating animals randomly with drug or vehicle 15 mins prior to aconitine infusion and comparing the dose of aconitine necessary to induce ventricular arrhythmias in treatment groups with that of control groups. The compounds in accordance with the invention were administered as the mesylate or hydrochloride salt prepared immediately before use in a 5% dextrose solution. All drugs were administered via a femoral venous cannula in a dose volume of 0.5 ml.

Results

Intravenous administration of aconitine to the anaesthetised rat rapidly elicited ventricular extrasystoles of both monofocal and multifocal origin. All animals succumbed to a rapid ventricular tachycardia or ventricular fibrillation. The dose required to elicit ventricular tachycardia (10 consecutive beats) or ventricular fibrillation in control animals was 19.95±0.6 (n=56) Pretreatment of anaesthetised rats with either quinidine, procainamide, phenytoin, propranolol, lidocaine or verapamil increased the amount of aconitine required to elicit the same ventricular arrhythmia as that occurring in control animals (see Table 1). Pretreatment with these standard anti-arrhythmic agents also resulted in significant reductions in the resting diastolic blood pressure (Table 1).

Pretreatment with any of the compounds of the invention resulted in a dose-dependent increase in the amount of aconitine required to elicit ventricular arrhythmias.

TABLE 1

The effect of some standard anti-arrhythmic agents and some compounds in accordance with the invention on increasing the dose of aconitine required to induce ventricular arrhythmias in anaesthetised rats.

| Anti-arrhythmic agent (numbers refer to Chemical Examples above) | Dose mg/kg (i.v.) | % increase in DBP in aconitine to elicit VT/VF | % decrease in DBP |
|---|---|---|---|
| Quinidine | 10 | 8 | 43 |
| Procainamide | 20 | 11 | 22 |
| Phenytoin | 10 | 19 | 4 |
| Propranolol | 1 | 51 | 0 |
| Lidocaine | 10 | 44 | 1 |
| Verapamil | 1 | 84 | 68 |
| 1 | 1 | 29 | 11 |
| 2 | 5 | 440 | 10 |
| 3 | 1 | 144 | 8 |
| 4 | 1 | 490 | 13 |
| 5 | 5 | 30 | 5 |
| 6 | 5 | 149 | 1 |

TABLE 1-continued

The effect of some standard anti-arrhythmic agents and some compounds in accordance with the invention on increasing the dose of aconitine required to induce ventricular arrhythmias in anaesthetised rats.

| Anti-arrhythmic agent (numbers refer to Chemical Examples above) | Dose mg/kg (i.v.) | % increase in DBP in aconitine to elicit VT/VF | % decrease in DBP |
| --- | --- | --- | --- |
| 7 | 5 | 106 | 13 |
| 8 | 10 | 51 | 8 |
| 9 | 1 | 32 | 4 |
| 10 | 1 | 225 | 3 |
| 11 | 1 | 33 | 7 |
| 12 | 1 | 14 | 5 |
| 13 | 1 | 246 | 1 |
| 14 | 1 | 8 | 2 |
| 15 | 1 | 12 | 5 |
| 16 | 1 | 15 | 3 |
| 17 | 1 | 154 | 3 |
| 18 | 1 | 46 | 1 |

Example B

Guinea-pig right ventricular muscle preparation: (Campbell, Brit.J.Pharmac., 1982, 77, 541–548)

Strips of right ventricle excised from male guinea-pigs were electrically stimulated at a frequency of 1 Hz with punctate, bipolar silver wire electrodes. Preparations were superfused with a modified Tyrodes solution containing the compound of Examples 1, 3 or 4 from 0 to $3 \times 10^{-4}$M. The effect of the compounds on the maximum rate of change of membrane potential during phase 0 of the action potential ($V_{max}$) was observed.

Results

The compounds ($3 \times 10^{-7}$ to $3 \times 10^{-4}$M) caused dose-related decreases in the rate of rise of phase 0 of the cardiac action potential (see Table 2).

TABLE 2

$EC_{50}$ Values (50% reduction in $V_{max}$) for Compounds of Examples 1, 3 and 4

| Compound | $EC_{50}$ |
| --- | --- |
| Example 1 | $1.3 \times 10^{-4}$ M |
| Example 3 | $5.9 \times 10^{-6}$ M |
| Example 4 | $2.2 \times 10^{-6}$ M |

Example C

Toxicity

No marked toxicity was observed in beagle dogs when two to three times the effective dose of the compound of Example 4 was administered daily for 14 days. In rats, the acute $LD_{50}$ of the compound of Example 4 was found to be 8.34 mg/kg (i.v.) and 25.5 mg/kg (s.c.).

PHARMACEUTICAL EXAMPLES

Example P1

Tablet

| Ingredient | Amount per tablet |
| --- | --- |
| 5(3)-Amino-6-(2,3-dichlorophenyl)-2,3(2,5)-dihydro-3(5)-imino-2-isopropyl-1,2,4-triazine | 35.0 mg |
| Lactose | 200 mg |
| Maize Starch | 50 mg |
| Polyvinylpyrrolidine | 4 mg |
| Magnesium Stearate | 4 mg |

The drug was mixed with the lactose and starch and granulated with a solution of the polyvinylpyrrolidone in water. The resultant granules were dried, mixed with magnesium stearate and compressed to give tablets of average weight 293 mg.

Example P2

Tablet

| Ingredient | Amount per Tablet |
| --- | --- |
| Compound of Formula (I) | 35.0 mg |
| Lactose | 110.0 mg |
| Corn Starch, Pregelatinized | 2.5 mg |
| Potato Starch | 12.0 mg |
| Magnesium stearate | 0.5 mg |

The active compound was finely ground and intimately mixed with powdered excipients lactose, corn starch and magnesium stearate. The following was then compressed to afford a tablet weighing 160 mg.

Example P3

Injection

| Ingredient | Amount per ampoule |
| --- | --- |
| Compound of formula (I) | 35.0 mg |
| Water for Injections, q.s. | 1.0 mL |

The finely ground active compound was dissolved in the water for injections. The solution was filtered and sterilized by autoclaving.

Example P4

Suppository

| Ingredient | Amount per suppository |
| --- | --- |
| Compound of formula (I) | 35.0 mg |
| Cocoa Butter, or Wecobee TM Base q.s. | 2.0 g |

Wecobee is a trademark and is a hydrogenated fatty carboxylic acid.

The finely ground active compound was mixed with the melted suppository base (either Cocoa Butter or Wecobee TM base), poured into moulds and allowed to cool to afford the desired suppositories.

Example P5

Syrup

| Ingredient | Amount per 5 mL |
| --- | --- |
| Compound of formula (I) | 35.0 mg |
| Ethanol | 0.3 mg |
| Sucrose | 2.0 mg |
| Methylparaben | 0.5 mg |
| Sodium Benzoate | 0.5 mg |
| Cherry Flavour | q.s. |
| Colouring | q.s. |
| Water | q.s. to 5.0 mL |

Ethanol, sucrose, sodium benzoate, methylparaben and flavouring were combined in 70% of the total batch quantity of water. Colouring and the active compound were dissolved in the remaining water, then the two solutions were mixed and clarified by filtration.

Example P6

Capsule

| Ingredient | Amount per Capsule |
|---|---|
| Compound of formula (I) | 35.0 mg |
| Lactose | 440.0 mg |
| Magnesium Stearate | 5.0 mg |

The finely ground active compound was mixed with the powdered excipients lactose, corn starch and stearate and packed into gelatin capsules.

What we claim is:

1. A compound of formula I:

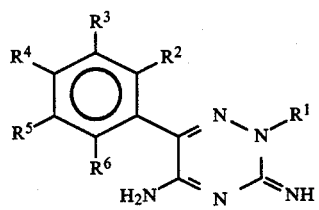

or the 5-imino tautomer thereof or a salt of either, wherein $R^1$ is selected from $C_{1-10}$ alkyl, $C_{2-10}$ alkenyl, $C_{2-10}$ alkynyl and $C_{1-10}$ cycloalkyl, and $R^2$ to $R^6$ are independently selected from hydrogen, halogen, $C_{1-6}$ alkyl, alkenyl, alkynyl or alkoxy (all optionally substituted by one or more of halogen, hydroxy and aryl), amino, amino mono- or di-substituted with lower alkyl alkenyloxy, lower alkanoyl, acyloxy, cyano, nitro, phenyl and alkylthio groups or any adjacent two of $R^2$ to $R^6$ are linked to form a (—CH=CH—CH=CH—) group, in the above the total number of carbon atoms in $R^2$ to $R^6$ is less than eight.

2. A compound according to claim 1 wherein $R^1$ is an unsubstituted $C_{1-6}$ alkyl group.

3. A compound according to claim 2 wherein $R^1$ is selected from methyl, n-propyl and isopropyl.

4. A compound according to claim 1 wherein the total number of carbon atoms in $R^2$ to $R^6$ is less than eight.

5. A compound according to claim 4 wherein $R^2$ is other than hydrogen.

6. A compound according to claim 5 wherein $R^2$ and $R^3$ are each chloro and $R^4$, $R^5$ and $R^6$ are each hydrogen.

7. 5(3)-Amino-6-(2,3-dichlorophenyl)-2,3(2,5)-dihydro-3(5)-imino-2-isopropyl-1,2,4-triazine or a salt thereof.

8. A pharmaceutical composition comprising a non-toxic effective antiarrhythmic amount of a compound of claim 1 or a salt thereof and a pharmaceutically acceptable carrier.

9. A composition according to claim 8, wherein the said compound is 5(3)-Amino-6-(2,3-dichlorophenyl)-2,3(2,5)-dihydro-3(5)-imino-2-isopropyl-1,2,4-triazine or a salt thereof.

10. A method of treating a human being who has been diagnosed as suffering from arrhythmia comprising the administration to said human being of a composition according to claim 8.

11. A method according to claim 10 wherein the compound is 5(3)-amino-6-(2,3-dichlorophenyl)-2,3(2,5)-dihydro-3(5)-imino-2-isopropyl-1,2,4-triazine.

12. The methanesulphonate salt of 5(3)-amino-6-(2,3-dichlorophenyl)-2,3(2,5)-dihydro-3(5)-imino-2-isopropyl-1,2,4-triazine.

13. A pharmaceutically acceptable acid addition salt of 5(3)-amino-6-(2,3-dichlorophenyl)-2,3(2,5)-dihydro-3(5)-imino-2-isopropyl-1,2,4-triazine.

14. The salt of claim 13 which is the hydrochloride salt.

15. 5(3)-amino-6-(2,3-dichlorophenyl)-2,3(2,5)-dihydro-3(5)-imino-2-isopropyl-1,2,4-triazine.

16. A method of treating a human who has been diagnosed as suffering from arrhythmia comprising the administration to said human of an effective antiarrhythmia treatment amount of 5(3)-amino-6-(2,3-dichlorophenyl)-2,3(2,5)-dihydro-3(5)-imino-2-isopropyl-1,2,4-triazine or a pharmaceutically acceptable salt thereof.

17. The method of claim 16 in which the methanesulphate salt is administered.

18. The method of claim 16 in which the hydrochloride salt is administered.

19. A pharmaceutical composition comprising 5(3)-amino-6-(2,3-dichlorophenyl)2,3(2,5)-dihydro-3(5)-imino-2-isopropyl-1,2,4-triazine or a pharmaceutically acceptable salt thereof together with a pharmaceutically acceptable carrier therefor.

20. A method of treating cardiovascular disorders by the administration of a composition of claim 19.

* * * * *